United States Patent
Huff et al.

(10) Patent No.: US 6,714,856 B2
(45) Date of Patent: Mar. 30, 2004

(54) ETHANOL CONTENT RATIONALITY FOR A FLEXIBLE FUELED VEHICLE

(75) Inventors: Shean P Huff, Knoxville, TN (US); John M Prevost, Spring Arbor, MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 223 days.

(21) Appl. No.: 09/982,060

(22) Filed: Oct. 18, 2001

(65) Prior Publication Data

US 2003/0075119 A1 Apr. 24, 2003

(51) Int. Cl.[7] .................................................. G06G 7/70
(52) U.S. Cl. .......................... 701/114; 123/1 A; 73/116
(58) Field of Search ................................ 123/689, 696, 123/699, 1 A, 478, 575, 479; 701/114; 73/116

(56) References Cited

U.S. PATENT DOCUMENTS

| | | | | |
|---|---|---|---|---|
| 5,014,670 A | * | 5/1991 | Mitsumoto | 123/406.15 |
| 5,881,703 A | * | 3/1999 | Nankee et al. | 123/686 |
| 5,957,094 A | | 9/1999 | Krausman et al. | 123/1 A |
| 6,000,367 A | | 12/1999 | Huff et al. | 123/1 A |
| 6,041,278 A | | 3/2000 | Kennie et al. | 701/103 |
| 6,298,838 B1 | * | 10/2001 | Huff et al. | 123/674 |

\* cited by examiner

*Primary Examiner*—Willis R. Wolfe
*Assistant Examiner*—Johnny H. Hoang
(74) *Attorney, Agent, or Firm*—Ralph E. Smith

(57) ABSTRACT

A method for checking the accuracy of an oxygen sensor based determination of the alcohol content of the fuel of a flexible fueled vehicle. Following the addition of fuel to the flexible fueled vehicle two alcohol concentration possibilities are calculated. The two alcohol concentration possibilities are then used to calculate thresholds for the determining if the oxygen sensor based determination falls within the thresholds. If the oxygen sensor based determination does not fall within the thresholds then action is taken to counteract an inaccurate determination of alcohol concentration.

10 Claims, 3 Drawing Sheets

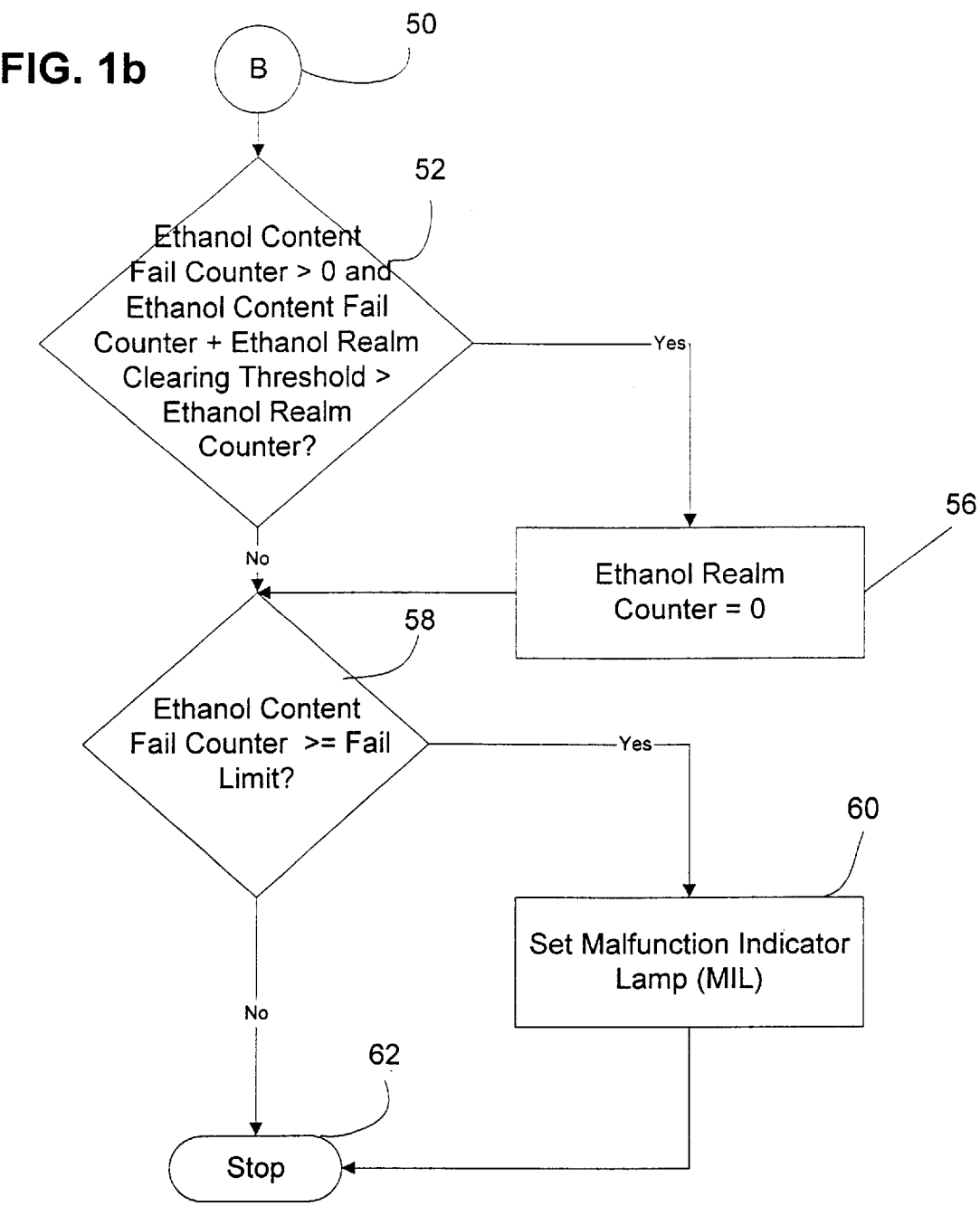

ETHANOL CONTENT RATIONALITY FOR A FLEXIBLE FUELED VEHICLE

FIELD OF THE INVENTION

The present invention relates generally to fuel control systems and, more particularly, to a system for rationalizing the alcohol content of the fuel of a flexible fueled vehicle.

BACKGROUND OF THE INVENTION

Alternative fuel vehicles are becoming commonplace in response to environmental and energy conservation concerns. Alcohol in the form of ethanol or methanol is combined in various percentages with gasoline to produce one type of alternative fuel. The vehicles capable of operating on more than one blend of gasoline and alcohol are referred to as flexible fuel vehicles. These vehicles may have some capability to adjust various engine operating parameters to compensate for the effects of one alcohol fuel blend over another including the possible use of gasoline unblended with alcohol.

This includes adjustment to the air to fuel mixture in order to maximize engine performance and to fully burn the fuel in use. The ideal air to fuel ratio in an internal combustion engine is typically considered to be the ratio of mass flow rate of air to mass flow rate of fuel inducted by an internal combustion engine to achieve conversion of the fuel into completely oxidized products. The chemically correct ratio corresponding to complete oxidation of the products is called stoichiometric. If the air/fuel ratio is less than stoichiometric, an engine is said to be operating rich, i.e., too much fuel is being burned in proportion to the amount of air to achieve perfect combustion. Likewise, if the air/fuel ratio is greater than stoichiometric, an engine is said to be operating lean, i.e., too much air is being burned in proportion to the amount of fuel to achieve perfect combustion. Since alcohol fuels require a lower air/fuel ratio than pure gasoline at stoichiometric, the engine must be compensated for in the rich direction. The amount of compensation increases as the percentage of alcohol in the fuel increases. For example, an engine operating on E85 (a blend of 85% ethanol and 15% gasoline) requires approximately 1.4 times the amount of fuel relative to gasoline at stoichiometry due to a lower energy content of the ethanol.

Various prior art methods and systems are already disclosed for determining the amount or percentage of alcohol in the fuel of a flexible fuel vehicle. Some of these systems utilize a composition sensor to measure the composition of the fuel used. A problem with these composition sensor based systems is the advent of sensor failure or miscalculation. This could result in the engine control system receiving faulty data upon which the engine is operated.

Other systems "learn" the alcohol content of the fuel through an oxygen sensor in the exhaust system that measures the oxidation of combustion byproducts in the exhaust. A potential problem with these "learn" based systems is the effect of a malfunction of a component of the system that effects the combustion byproducts or even a malfunction of the oxygen sensor. For example, a clogged fuel filter or injector drift could effect the learned determination of the alcohol content by causing a faulty fuel system and resulting in lean combustion. A system could under these and other circumstances learn into the alcohol realm and effect the engine control system.

Therefore, there is a need for a system that will rationalize the alcohol content without reliance on a fuel composition sensor. Further, a system is needed that will rationalize the alcohol content as a backup to any sensor or learned result.

SUMMARY OF THE INVENTION

It is therefore an object of the invention, a rationality system, to rationalize (i.e. check for accuracy) the alcohol content of the fuel in a flexible fueled vehicle. It is a further object to provide a backup to a learned (i.e. oxygen sensor) or fuel composition sensor based system in determining the possible alcohol content of the fuel. A further object of the invention is to allow activation of warning systems and/or other action if the system detects fault in the determination of the alcohol concentration in the fuel.

In operation the invention is activated by a triggering event such as an addition of fuel to the fuel tank. The rationality system then calculates the possible concentrations of alcohol in the fuel based on the possible fuels added. Next, the rationality system compares the alcohol content as determined by a learned based system or a sensor based system to the possible concentrations of alcohol. If the determined alcohol content is too far from the possible concentrations of alcohol then a fail counter is incremented to show a failure to properly determine the fuel alcohol content. If the fail counter reaches a predetermined level then action is taken to warn the vehicle operator of the fault. Diagnostic systems may also be enabled or disabled depending on whether the alcohol content of the fuel is within the alcohol realm.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1b is a continuing flowchart of the rationalization system.

DETAILED DESCRIPTION OF THE PREFERRED EMBODIMENTS

Figure 1:
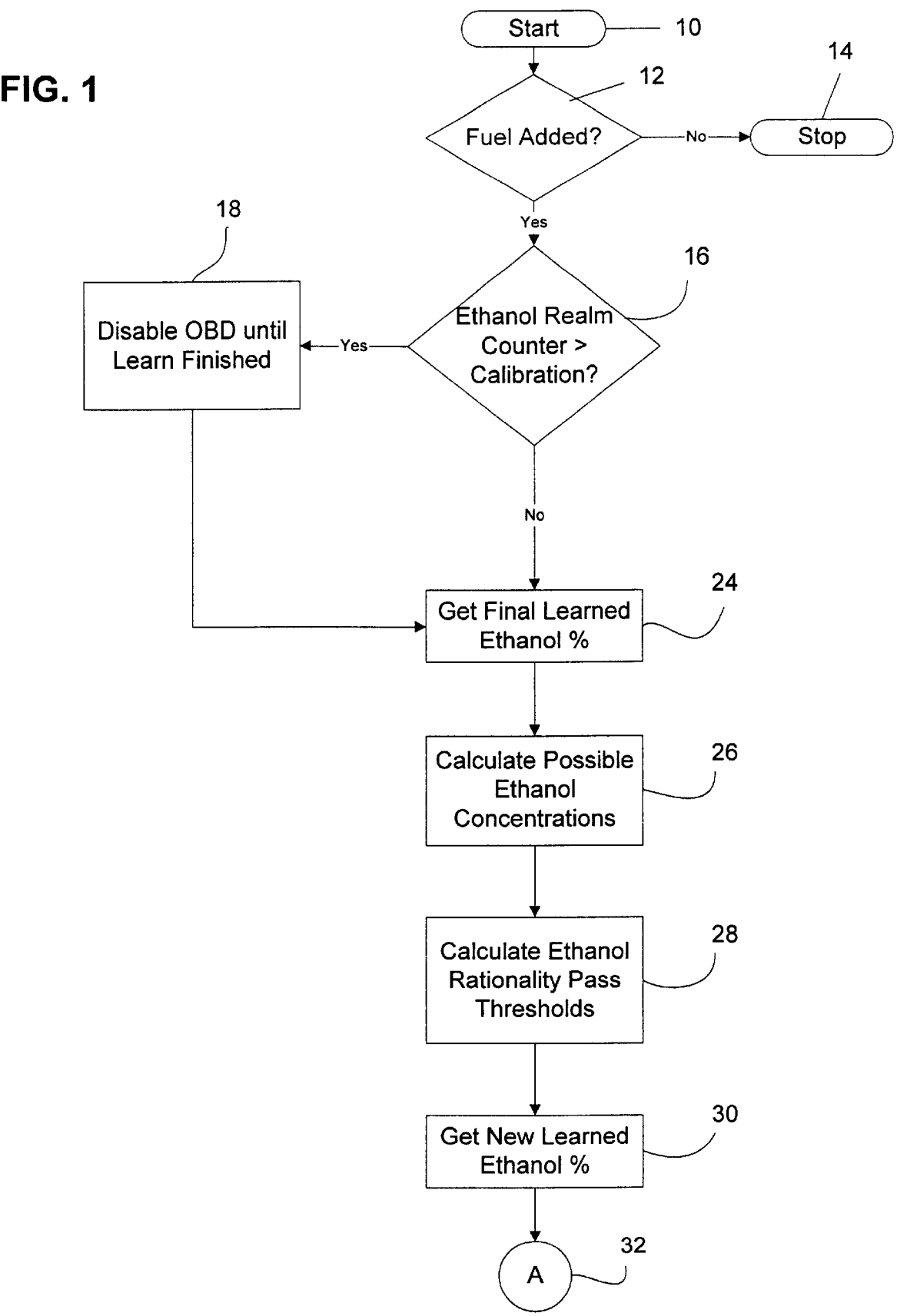
FIG. 1 is a flowchart of a preferred embodiment of the rationalization system.

The following description of the preferred embodiment(s) is merely exemplary in nature and is in no way intended to limit the invention, its application, or uses. The diagrams and discussion refer generally to ethanol and specifically to an ethanol in the form of E85 (i.e. 85% ethanol and 15% gasoline) as a type of alcohol mixed with gasoline to produce an alternative fuel. This is not intended as a limitation however, as it should be apparent to one skilled in the art that the rationalization system would equally apply to other alternative fuels including other alcohol based fuel blends such as methanol based fuel blends.

The rationalization system process is initiated in step 10. In step 12 the rationalization system checks for the addition of fuel. This may include comparing a detected change in fuel volume to a minimum fixed amount or a percentage or both in order to limit the system to activation based on a certain minimal change in fuel volume. As an alternative the system can be activated based on a simple change in fuel volume.

If the system determines that insufficient fuel has been added at step 12, the method advances to step 14 and ends pending a subsequent execution thereof. For example, the method could be run at each start-to-run transition event. Still referring to step 12, if the system determines that fuel has been added, the method continues to step 16.

In step 16 the system compares an ethanol realm counter with a calibrated value. The ethanol realm counter counts the number of times that the system determines that the fuel in the vehicle contains a specified minimum percentage of ethanol that qualifies as operating in the ethanol realm. For example, the ethanol realm can be set at a minimum value of 30% meaning the fuel in the vehicle must be at least 30% ethanol to be considered in the ethanol realm. The calibrated value is also a specified number corresponding to a minimum number of times that the system must determine the fuel to contain 30% ethanol in order to disable certain functions until an ethanol "learn" is completed. If the ethanol realm counter is greater than the calibrated value at step 16 then it is considered that the fuel system is known to use ethanol. In this event the method advances to step 18 where the system disables onboard diagnostics (OBD) until the fuel system "learns" the amount of alcohol in the system. An example of some of the OBD diagnostics that may be disabled include the fuel system monitor, oxygen sensor monitor, and misfire monitor.

An ethanol "learn" may be based on an oxygen sensor in the exhaust system of the vehicle. The ethanol learn based on an oxygen sensor may generally be characterized as measuring the level of oxygen in the combustion byproducts and calculating a percentage concentration of ethanol based on this measure.

If the ethanol realm counter is less than the calibrated value at step 16 then the method moves to step 24 where the final learned ethanol percent is retrieved from memory. The final learned percent is the learned ethanol percent from the last time that it was determined. Next, in step 26, the possible concentrations of ethanol are calculated. These calculations are as follows:

A first percent possibility, assuming that a first percent of ethanol is a lower percent of ethanol, such as less than 50 percent, or even 0 percent was added, equals the change in fuel volume multiplied by lower percent of ethanol (as an example 15%) plus the pre-fill fuel volume multiplied by the final learned ethanol percent then divided by the post-fill fuel volume. If the lower percent of ethanol is 0 percent then the first percent possibility equals the pre-fill fuel volume multiplied by the final learned ethanol percent divided by the post-fill fuel volume.

A second percent possibility, assuming that a second percent of ethanol is a higher percent of ethanol, such as greater than 50 percent, or even 85 percent, was added equals the change in fuel volume multiplied by 85% (as an example of E85) plus the pre-fill fuel volume multiplied by the final learned ethanol percent then divided by the post-fill fuel volume.

In these calculations an E0-possiblity, as a first percent possiblity, represents the possibility of zero percent ethanol fuel was added to the tank. The E0-possibility is calculated by taking the pre-fill fuel volume which is the volume of fuel prior to the most recent addition of fuel and multiplying it with the ethanol percent that is the final learned ethanol percent. This calculation is then divided by the total fuel volume.

In the above calculations an E85-possiblity represents the possibility of 85 percent ethanol fuel was added to the tank. For the E85-possibility calculation, the delta fuel volume is the change in volume between the pre-fill fuel volume and the volume following the addition of fuel. The delta fuel volume is multiplied by 85 percent representing the percentage of alcohol in E85 fuel. This calculation is then added to the calculation of pre-fill fuel volume multiplied by the ethanol percent. The pre-fill fuel volume is the volume of fuel prior to the most recent addition of fuel. The ethanol percent is again, the final learned ethanol percent. This entire calculation is then divided by the current fuel volume in order to determine the E85-possibility.

Next, in step 28 the ethanol content rationality thresholds are calculated. The thresholds are calculated as follows:

A first ethanol rationality pass threshold, for instance when less than 50% ethanol was added to the tank, such as 0 percent ethanol, equals the final learned ethanol percent minus the result of the final learned ethanol percent minus the first ethanol percent possibility multiplied by the ethanol content rationality pass threshold fraction.

A second ethanol rationality pass threshold, for instance when more than 50% ethanol was added to the tank, such as 85 percent ethanol, equals the final learned ethanol percent plus the result of the second percent possibility minus the final learned ethanol percent multiplied by the ethanol content rationality pass threshold fraction.

For calculation of an E0-rationality-pass-threshold, as a first ethanol rationality pass threshold, the starting ethanol percent is again the final learned ethanol percent. The E0-possibility is the percent possibility calculation as determined in step 26. The ethanol content rationality pass threshold fraction is a fixed value that is used in the calculation to factor in a degree of freedom from the base calculation.

For calculation of an E85-rationality-pass-threshold, as a second ethanol rationality pass threshold, the starting ethanol percent is the final learned ethanol percent. The E85-possibility is the percent possibility calculation as determined in step 26. The ethanol content rationality pass threshold fraction is preferably the same fixed value as in the preceding equation.

Moving to step 30 a new learned ethanol percent is determined. This may be performed by an oxygen sensor in the exhaust system of the vehicle. The oxygen sensor allows for calculating a percent of ethanol by sensing a rich or lean level of combustion. After this step the logic flows through connector 32 to FIG. 1*a*.

Figure 1A:
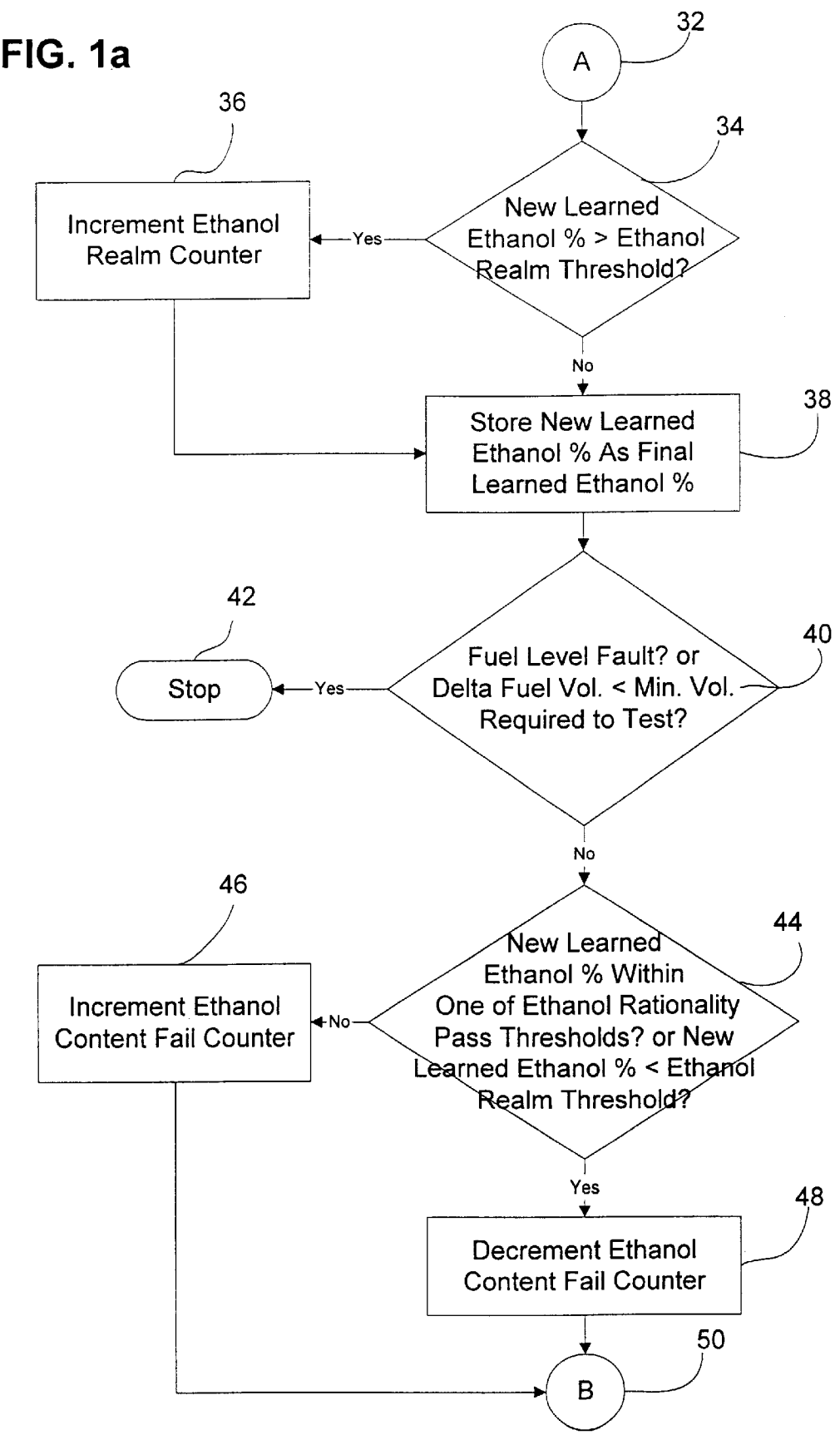
FIG. 1a is a continuing flowchart of the rationalization system.

Referring now to FIG. 1*a*, in decision block 34 the new learned ethanol percent is compared to the ethanol realm threshold. The ethanol realm threshold is again the fixed percentage of ethanol (e.g. 30%) determined to represent the minimal percentage of ethanol necessary to consider that the fuel system is within an ethanol realm. If the learned ethanol percent in step 34 exceeds the ethanol realm threshold, then in step 36 an ethanol realm counter is incremented. The ethanol realm counter keeps track of each time that the fuel system is found in the ethanol realm. Next, in step 38 the new learned ethanol percent is stored as the final learned ethanol percent for future calculations.

In decision block 40, the system checks for a fuel level fault or if the change in fuel volume is less than the minimum volume required to perform the ethanol content rationality determination. In the event of a fuel level fault or a change in fuel volume less than the minimum volume required, then in step 42 the system is stopped. Otherwise, the system logic proceeds in decision block 44 where the learned ethanol percent is compared to the ethanol rationality pass thresholds calculated in step 28. The check of decision block 40 differs from that of decision block 12 by setting a higher minimum volume requirement or other more restrictive requirements than in decision block 12. For example, the minimum change in fuel volume may be 40% in step 40 while the minimum change in fuel volume may be 15% in step 12.

In step 44 a check is performed to determine if the new learned ethanol percent is within one of the first or second ethanol rationality pass thresholds or if the new learned ethanol percent is less than the ethanol realm threshold. The ethanol rationality pass thresholds were calculated in step 28. The first part of step 44 involves comparing the new learned ethanol percent to the first and second ethanol rationality pass thresholds from step 28. If the new learned ethanol percent is less than the first ethanol rationality pass threshold or greater than the second ethanol rationality pass threshold then the new learned ethanol percent is within one of the ethanol rationality thresholds. Otherwise, the new learned ethanol percent is outside of the ethanol rationality pass thresholds and the new learned ethanol percent has failed the ethanol rationality.

Still referring to step 44 the ethanol realm threshold is the same as identified in step 34. If the new learned ethanol percent is within the ethanol rationality pass thresholds or the new learned ethanol percent is less than the ethanol realm threshold (e.g. 30%) then the ethanol content fail counter in step 48 is decremented. Alternatively, the ethanol content fail counter is incremented in step 46. Next, in connector block 50 the logic of the system continues to FIG. 1b.

Referring now to FIG. 1b, in decision block 52 the ethanol content fail counter is compared to zero. If the ethanol content fail counter is greater than zero, and if the ethanol content fail counter plus the ethanol realm clearing threshold are greater than the ethanol realm counter then the system logic moves to decision block 56 where the ethanol realm counter is set to zero. In step 52 the ethanol realm clearing threshold is a fixed value for example 3 representing a threshold number of times the ethanol realm counter is above the ethanol content fail counter before the ethanol realm counter is cleared to zero. Step 52 is intended to protect the gasoline only user by not disabling OBD monitoring when the logic of the system reaches step 16 during the next cycle of the rationalization system.

Next, in decision block 58 the ethanol content fail counter is compared to the fail limit. The fail limit is a fixed value representing the number of times of failure before determining that action should be taken. If the ethanol content fail counter is greater than or equal to the fail limit, then in step 60 the malfunction indicator lamp is set. If the ethanol content fail counter is less than the fail limit at decision block 58, or after setting the process of block 60, the method continues to terminator 62. The process for the system stops in step 62.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for checking the accuracy of a determined alcohol content of fuel for a flexible fueled vehicle, comprising:

calculating at least two alcohol concentration possibilities based on at least two possible fuel types wherein the at least two possible fuel types have different alcohol concentrations;

calculating thresholds for the at least two alcohol concentration possibilities;

comparing the determined alcohol content to the thresholds; and assuming an error in the determined alcohol content of the flexible fueled vehicle if the determined alcohol content is outside the thresholds.

2. The method of claim 1 further comprising:

checking for the addition of fuel to the flexible fueled vehicle before calculating the at least two alcohol concentrations.

3. The method of claim 1 wherein the determined alcohol content is based on an oxygen sensor reading.

4. The method of claim 1 wherein the thresholds are a calibrated fraction of the difference between the determined alcohol content and the at least two alcohol concentration possibilities.

5. The method of claim 1 further comprising:

setting a fail threshold counter to a predetermined value;

providing a fail counter for counting the number of times that the error in the determined alcohol content occurs;

incrementing the fail counter for the error in the determined alcohol content; and comparing the fail counter to fail threshold counter wherein a signal is set if the fail counter exceeds the fail threshold.

6. The method of claim 1 further comprising:

providing an alcohol realm threshold to establish a baseline measure of alcohol in the fuel;

setting the alcohol realm threshold to a value representing a minimum percentage of alcohol in the fuel to be considered in the alcohol realm;

providing an alcohol realm threshold counter to count the number of times that the alcohol content of the fuel exceeds the alcohol realm threshold; and comparing the determined alcohol content of fuel to the alcohol realm threshold and incrementing the alcohol realm threshold counter if the determined alcohol content exceeds the alcohol realm threshold.

7. The method of claim 6 further comprising:

delaying a diagnostic system operation if the determined alcohol content exceeds the alcohol realm threshold.

8. The method of claim 6 further comprising:

delaying a diagnostic system operation until a new determined alcohol percent is obtained if the determined alcohol content exceeds the alcohol realm threshold.

9. The method of claim 6 further comprising:

providing an ethanol counter limit for setting a minimum threshold of times in the alcohol realm; and delaying a diagnostic system operation if the alcohol realm counter exceeds the alcohol counter limit.

10. A method for rationalizing a determined fuel blend of a flexible fuel in a fuel tank of a flexible fueled vehicle comprising:

providing a first fuel blend possibility wherein the first fuel blend possibility comprises at least two fuel components wherein a first component is present in the fuel blend in a greater proportion than a second component;

providing a second fuel blend possibility wherein the second fuel blend possibility comprises the at least two fuel components wherein the first component is present in the second fuel blend possibility in a lesser proportion than the second component;

calculating a first threshold for the first fuel blend possibility;

calculating a second threshold for the second fuel blend possibility;

comparing the determined fuel blend to the first threshold and to the second threshold; and recognizing an error in the determined fuel blend if the determined fuel blend is greater than the first threshold or less than the second threshold.

* * * * *